United States Patent [19]

Smith

[11] 4,255,172
[45] Mar. 10, 1981

[54] JET IMPACTION PRESEPARATOR

[75] Inventor: Michael L. Smith, Atlanta, Ga.

[73] Assignee: Andersen Samplers Inc., Atlanta, Ga.

[21] Appl. No.: 94,291

[22] Filed: Nov. 14, 1979

Related U.S. Application Data

[63] Continuation-in-part of Ser. No. 10,391, Feb. 8, 1979, abandoned, and Ser. No. 13,401, Feb. 21, 1979.

[51] Int. Cl.³ .................................................. B01D 53/30
[52] U.S. Cl. ........................................ 55/270; 55/319;
55/446; 55/465; 73/28
[58] Field of Search ................ 55/319, 270, 321, 446,
55/465–466; 73/28, 29, 421.5 R

[56] References Cited

U.S. PATENT DOCUMENTS

| | | | |
|---|---|---|---|
| 2,538,116 | 6/1951 | May | 73/28 |
| 3,001,914 | 9/1961 | Andersen | 73/28 |
| 3,606,738 | 9/1971 | Kraus, Jr. | 55/446 |
| 3,616,627 | 11/1971 | Everett el al. | 55/465 |
| 3,693,457 | 9/1972 | Pilat | 73/28 |
| 3,795,135 | 3/1974 | Andersen | 73/28 |
| 3,953,182 | 4/1976 | Roth | 73/28 |

FOREIGN PATENT DOCUMENTS 565256 4/1957 Italy .......................................... 55/465

Primary Examiner—Charles N. Hart
Assistant Examiner—E. Rollins Cross
Attorney, Agent, or Firm—B. J. Powell

[57] ABSTRACT

A preseparator for connection to the sampling inlet of a particle sizing sampler to preseparate those particles from the gaseous medium with particle diameters above the particle diameter acceptance range of the sampler which is characterized by a housing defining a preseparating chamber therein, an impaction plate dividing the preseparating chamber into two subchambers, a preimpaction nozzle which forces a jet of the gaseous medium against the impaction plate to separate those particles above the particle diameter acceptance range of the sampler by jet impaction and at least one exit passage which extends through the impaction plate with an inlet spaced from the impaction plate a distance greater than the distance between the outlet on the preimpaction nozzle and the impaction plate.

10 Claims, 8 Drawing Figures

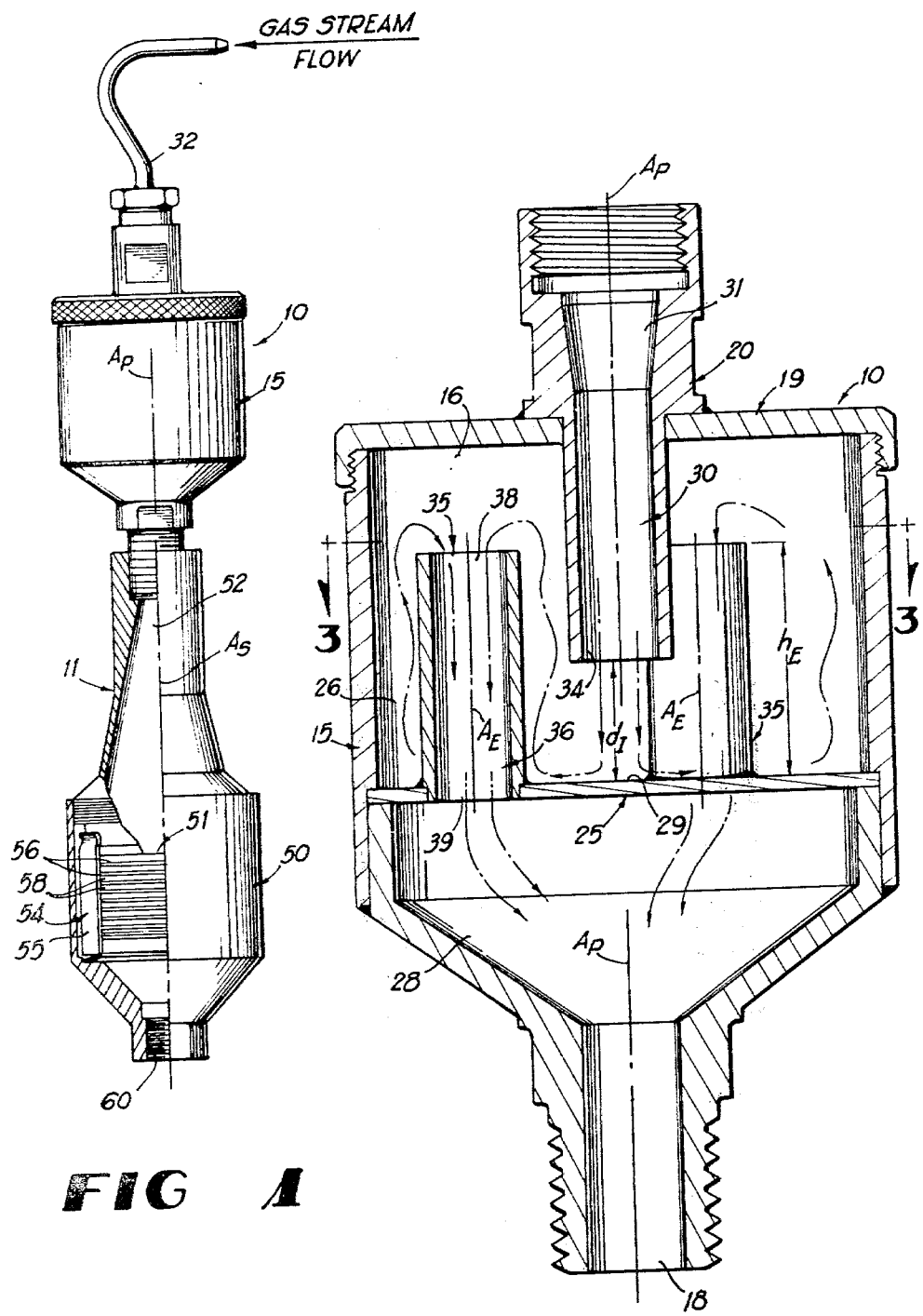

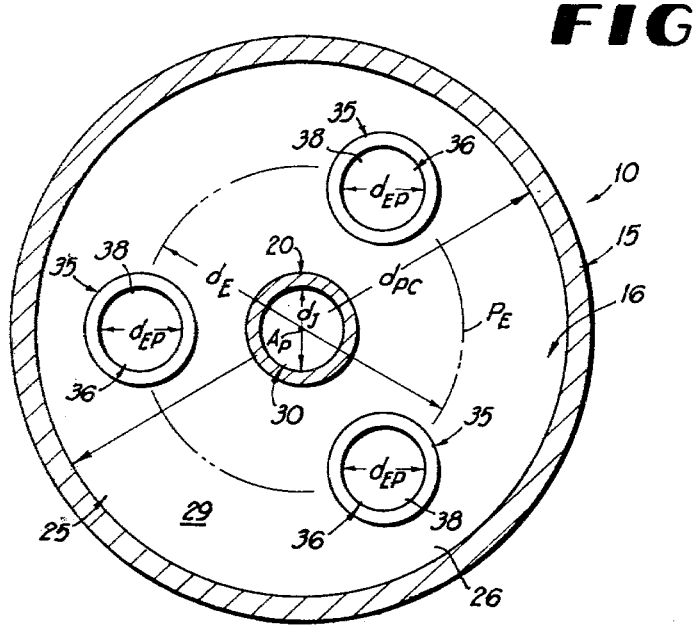
FIG 3
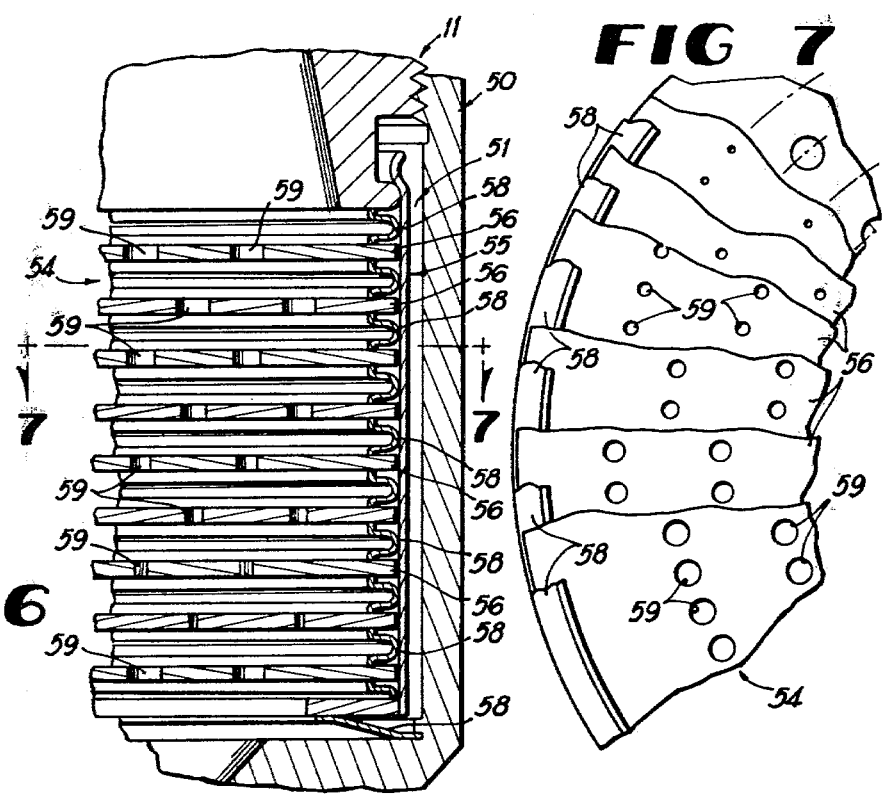
FIG 6
FIG 7

FIG 8

JET IMPACTION PRESEPARATOR

CROSS-REFERENCE TO RELATED APPLICATIONS

This application is a continuation-in-part of my copending applications Ser. No. 010,391, filed Feb. 8, 1979, now abandoned, and Ser. No. 013,401, filed Feb. 21, 1979.

BACKGROUND OF THE INVENTION

Various particle sizing samplers are available on the market today for sampling particles according to size which are bourne by a gaseous medium as air. These samplers are generally concerned with those size particles entrained in a gaseous medium which are harzardous to humans because they are breathable. Because sampling devices are concerned only with breathable size particles, their sampling size range is generally for particles about ten microns or less in diameter. The volumeric flow rates through any particluar one of these particle sizing samplers may vary depending on the particular application, usually from less than one cfm to more than forty cfm.

One of the problems with these air samplers is that, many times, the gaseous medium being sampled contains some particles which are significantly larger in diameter than the particle size acceptance range of the samplers. When the gaseous medium being sampled contains these larger particles, the larger particles bounce off the impaction surface and reentrain themselves in the gas stream. These reentrained particles are subsequently separated out on the lower stages and thereby skew the size distribution data so as to make the particle size distribution and mass medium diameter appear smaller than it actually is.

Attemps have been made to preliminarily separate those particles from the gas stream just prior to passage through the particle sizing sampler which are significantly larger than the sampler particle size acceptance range such as the use of a small cyclone preseparator. Because the diameter of a cyclone at any given flow rate determines the size of the particles collected thereby, the required diameter of a cyclone used to preseparate only those particles with diameters significantly larger than those in the sampler particle size acceptance range frequently resulted in the required diameter of a preseparator cyclone being significantly larger than the diameter of the particle sizing sampler. In some instances, this has been a problem because the diameter of the sampler access openings through the ducts carrying the gases to be sampled is about the same diameter as the particle sizing samplers, thereby making it difficult to use a preseparator cyclone with the particle sizing sampler since the preseparator cyclone diameter may be larger than these access openings in the ducts through which the preseparator cyclone and the particle sizing sampler must be inserted to accurately sample the particles according to size. The only way to reduce the preseparator cyclone diameter is to reduce the flow rate through the sampler and this is frequently an undesirable alternative.

Another problem with preseparator cyclones is that there are no satisfactory theoretical formulations to predict the behavior of the cyclone at various gas temperatures and pressures. This makes it necessary to calibrate the cyclone empirically at every gas temperature and pressure combination which might be encountered in actual use. This calibration procedure is expensive to perform and makes cyclones less desirable as sampling instruments than impactors.

Another problem encountered when using prior art preseparators with particle sizing samplers is that the particles which were preseparated from the gas stream by the preseparator were sometimes undesirably reentrained in the gas stream and carried into the particle sizing sampler. This is especially a problem when sampling is being attempted under conditions where high grain loadings of the larger size particles in the gas stream being sampled were present. Another problem encountered in prior art preseparators is that the collection capacity of the preseparator was not sufficient to permit the preseparator and thus the particle sizing sampler to remain in the gase stream for the necessary length of time required for adequate sampling without distortion of the particle preseparation characteristics of the preseparator.

SUMMARY OF THE INVENTION

These and other problems and disadvantages associated with the prior art are overcome by the invention disclosed herein by providing a preseparator for use with a particle sizing sampler which can preseparate particles with diameters exceeding the acceptance range of the particle sizing sampler with which it is being used while being able to collect relatively large quantities of the preseparated particles with minimal reentrainment in the gas stream passing into the particle sizing sampler and without distortion of the preseparation characteristics of the preseparator. Further, the preseparator behaves in accordance with established impactor theoretical formulations, and its behavior can be accurately predicted at any given gas temperature and pressure combination. Further, the preseparator has a diameter which permits the preseparator to be inserted through the existing access openings in the ducts to permit access of the sampler.

According to the present invention, there is provided a preseparator for connection to the sampling inlet of a particle sizing sampler so that a gaseous medium is forced first through the preseparator to preseparate those particles from the gaseous medium above the particle diameter acceptance range of the particle sizing sampler and then through the particle sizing sampler to separate those particles within the diameter acceptance range of the sampler from the gaseous medium according to size which is characterized by a housing defining a preseparating chamber therein about a preimpaction central axis having an outlet therefrom connected to the sampling inlet of the particle sizing sampler; an impaction plate mounted in the preseparating chamber and dividing the chamber into an impaction subchamber and a discharge subchamber where the outlet communicates with the discharge subchamber; preimpaction nozzle means oriented generally normal to the impaction plate and defining at least one preimpaction jet passage therethrough having a nozzle inlet communicating with the gaseous medium to be sampled and a nozzle outlet communicating with the impaction subchamber, the nozzle outlet sized and located with respect to the impaction plate to cause those particles in the gaseous medium with effective particle diameters above the particle diameter acceptance range of the particle sizing sampler to be separated by jet impaction on the impaction plate within the impaction subchamber; and exit tube means defining at least one exit passage therethrough connecting the impaction subchamber with the discharge subchamber so that the gaseous medium passes from the impaction subchamber into the discharge subchamber through the exit passage with the exit passage having a passage inlet located in the impaction subchamber and spaced from the impaction plate a distance greater then the distance from nozzle outlet on the preimpaction nozzle means to the impaction plate. The relative sizes of the preimpaction jet passage and the impaction subchamber are selected so that the velocity of the gaseous medium passing through the impaction subchamber is no greater than one-tenth of the velocity of the gaseous medium passing through the preimpaction jet passage. The size of the impaction subchamber and the location of the passage inlet to the exit tube means are further selected so that the residence time of the gaseous medium in the impaction subchamber is at least 0.2 second. The relative sizes of the passage inlet to the exit passages and the preimpaction jet passage are selected so that the velocity of the gaseous medium through the passage inlet is no greater than one-half the velocity of the gaseous medium passing through the preimpaction jet passage.

BRIEF DESCRIPTION OF THE DRAWINGS

FIG. 1 is a side view of the preseparator of the invention installed on a particle sizing sampler;

FIG. 2 is an enlarged longitudinal cross-section view of the preseparator;

FIG. 3 is a transverse cross-sectional view taken along line 3—3 in FIG. 2;

FIG. 6 is an enlarged partial longitudinal cross-sectional view of the particle sizing sampler;

FIG. 7 is a partial transverse cross-sectional view taken along line 7—7 in FIG. 6; and FIG. 8 is a graph illustrating the particle separation characteristics of the preseparator.

Figure 4:
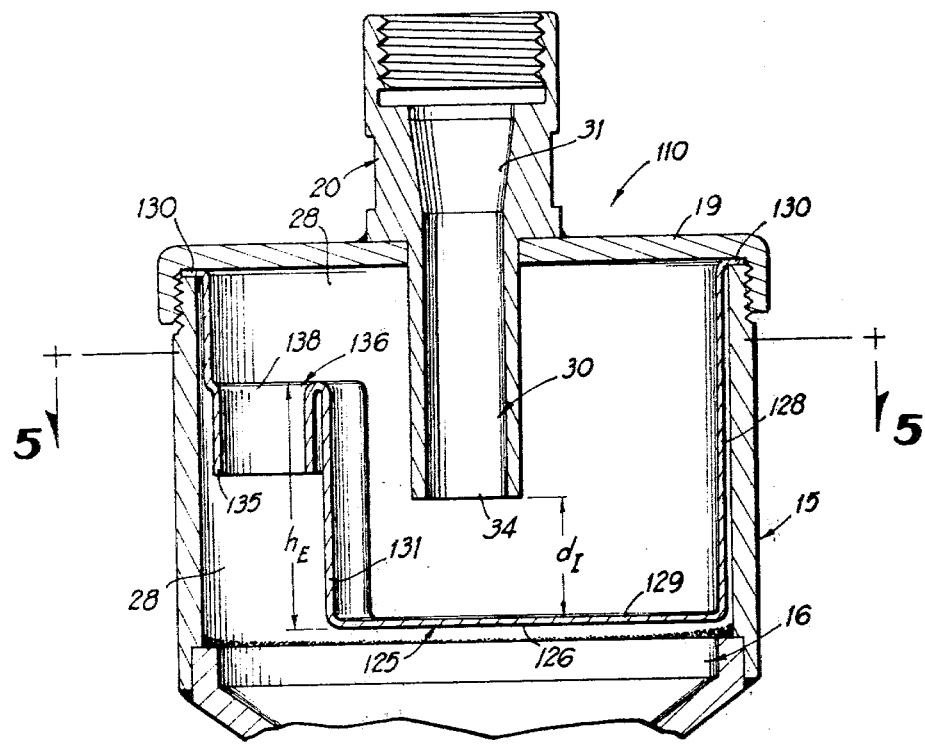
FIG. 4 is an enlarged longitudinal cross-sectional view showing an alternate embodiment of the preseparator.

These figures and the following detailed description disclose specific embodiments of the invention; however, it is to be understood that the inventive concept is not limited thereto and may be embodied in other forms.

DETAILED DESCRIPTION OF ILLUSTRATIVE EMBODIMENTS

Referring to FIGS. 1–3, it will be seen that the invention includes generally an impaction preseparator 10 connected to the inlet of a particle sizing sampler 11 so that the preseparator central axis $A_p$ is coaxial with the particle sizing sampler central axis $A_S$. The gaseous medium being sampled passes first through the preseparator 10 which separates the large particles that would clog the particle sizing sampler 11 and then the gaseous medium being sampled passes through the sampler 11 where entrained particles which would cause a health hazard are separated by size. The entire assembly is powered by a vacuum unit (not shown) which is connected to the discharge end of the sampler 11. Normally, the preseparator 10 has a cut point of about 10 microns while the sample 11 subdivides the particles remaining in the gaseous sampler after passage through preseparator 10 into further size distribution.

The impaction preseparator 10 as best seen in FIGS. 2 and 3 includes a generally cylindrical housing 15 defining a generally cylindrical preseparator chamber 16 therein of diameter $d_{PC}$ centered along the preseparator axis $A_p$ and opening onto one end of the housing 15 at its full diameter and communicating with an outlet passage 18 out through the opposite end of housing 15 into the sampler 11. The open end of the housing 15 is closed by a cap 19 which incorporates the preseparator impaction nozzle 20. The outside of housing 15 adjacent the open end is externally threaded to mate with the internal threads on cap 19 so that the cap 19 can be unscrewed from housing 15 to gain access to the preseparator chamber 16.

A circular impaction plate 25 is mounted on the housing 15 within the preimpaction chamber 16. The impaction plate 25 is oriented normal to the preseparator axis $A_p$ and separates the preimpaction chamber 16 into an impaction subchamber 26 facing the cap 19 and a discharge subchamber 28 which communicates with the outlet passage 18. That surface 29 of plate 25 facing the cap 19 serves as the preimpaction surface onto which the larger size particles in the gas stream are impacted to preseparate them from the gas stream prior to entry into the particle sizing sampler 11.

The preseparator impaction nozzle 20 mounted through cap 19 is arranged concentrically about the preseparator axis $A_p$, and defines a preimpaction jet passage 30 therethrough also concentric about axis $A_p$ and normal to the preimpaction surface 29. The inlet 31 to the jet passage 30 is outside the cap 19 and communicates with the gas stream through a pickup nozzle 32 such as the gooseneck nozzle illustrated whose inlet is oriented facing the oncoming gas stream and whose inlet axis is generally coaxial with the gas stream flow. The impaction outlet 34 from the jet passage 30 is located in the vicinity of the impaction surface 29 to cause those larger size particles in the gas stream passing out of the outlet 34 to impact on the surface 29 and be separated from the gas stream.

Figure 8:
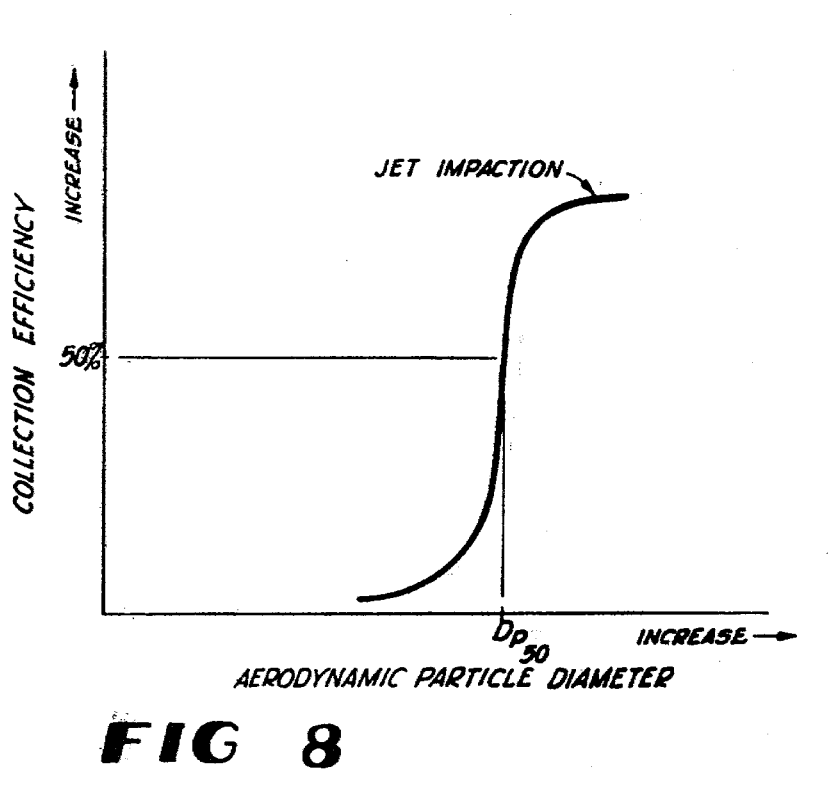

It should also be appreciated what the sampling industry considers as the effective particle cut diameter of a jet impaction particle separating mechanism. This type of mechanism exhibits a generally S-shaped collection efficiency versus particle diameter curve as illustrated in FIG. 8. The effective particle cut diameter is considered to be that size particle which is collected at a 50% collection efficiency and is referred to as generally by the reference $D_{P50}$. The particle sizes are the effective aerodynamic diameters of the particles and are usually expressed in microns.

As is well understood by those skilled in the art of separating particles from a gas stream by jet impaction, the effective particle cut diameter of the preseparator 10 is dependent primarily on the velocity of the jet stream of the gaseous medium issuing from the outlet of the jet passage 30, the distance the outlet of the jet passage 30 is located from the impaction surface, the viscosity of the gaseous medium, and the density of the particle. The velocity of the jet stream of the gaseous medium issuing from the jet passage 30 is dependent both on the cross-sectional size of the passage 30 and the gas volume flow rate through the passage 30. The viscosity of the gaseous medium cannot usually be varied to suit the sampling process and must be sampled as found. It should also be appreciated that the viscosity is also usually dependent on the temperature. As a result, the cross-sectional size of the passage 30 is determined based on some standard gas volume flow rate and viscosities found when sampling. Upon determination of the cross-sectional size of passage 30, the distance between the outlet of passage 30 and the impaction surface 29 can be determined. Normally, the selected standard gas volume flow rate through the preseparator 10 is about 0.75 cubic feet per minute (353.96 cubic centimeters per second) and the standard temperature used is about 70° F. (21.1° C.). Thus, to provide an effective particle cut diameter of about 11 microns under these conditions, the diameter $d_J$ of the passage 30 is selected at 0.48 inch (12.19 mm) while the distance $d_I$ between the impaction outlet 34 of the passage 30 and the preimpaction surface 29 on plate 25 is selected at 0.59 inch (14.94 mm). The preseparator 10 is usually further tested to provide a family of operating curves which allows compensation for variation in gas volume flow rates through the preseparator as well as different temperatures of the gaseous medium.

A plurality of exit tubes 35 is mounted on the impaction plate 25 so that the exit tube axes $A_E$ are oriented generally parallel to the preseparator central axis $A_p$. The number and location of the exit tubes 35 may be varied; however, there are three exit tubes 35 illustrated in FIGS. 2 and 3 and are circumferentially spaced about a circular path $P_E$ concentrically of the preseparator central axis $A_p$ with the circular path $P_E$ having a diameter $d_E$ as best seen in FIG. 3. The diameter $d_E$ is selected so that the center-to-center distance between each of the exit tubes 35 and the impaction nozzle 20 is at least as great as the diameter $d_J$ of the jet passage 30. The center-to-center distance illustrated is about one and one-half times the diameter $d_J$. Each of the exit tubes 35 defines an exit passage 36 of diameter $d_{EP}$ therethrough concentrically of the exit tube axis $A_E$ so that the inlet end 38 of each exit passage 36 is located within the impaction subchamber 26 while the outlet end 39 of the exit passage 36 opens into the discharge subchamber 28. Thus, it will be seen that each exit passage 36 extends through the impaction plate 25 so that the exit passage 36 provides communication through the impaction plate 25 from the impaction subchamber 26 to the discharge subchamber 28. Each of the exit tubes 35 projects from the impaction plate 25 into the impaction subchamber 26 to locate the inlet end 38 of exit passage 36 at a height $h_E$ as seen in FIG. 2 which is greater than the distance $d_I$ between the impaction outlet 34 of the preimpaction jet passage 30 and the preimpaction surface 29 and preferably about two times distance $d_I$.

Thus, it will be seen that the gaseous medium passing through preimpaction jet passage 30 in the preseparator impaction nozzle 20 is discharged in a jet stream out of the impaction outlet 35 so that the jet stream impinges against the preimpaction surface 29 on the impaction plate 25 to separate out the particles in the gaseous medium. After impingement against the preimpaction surface 29 on the impaction plate 25, the jet stream is deflected outwardly along the preimpaction surface 29 while deflecting the gas stream flow about 90° from the original path along the preseparator axis $A_p$. The deflected jet stream passing along the preimpaction surface 29 on the impaction plate 25 rapidly slows down because of the larger volume of subchamber 26. Eventually, the outwardly deflected gas stream turns away from the preimpaction surface 29 to move to the level of the inlet ends 38 of the exit passages 36 in exit tubes 35. The gaseous medium then turns back into the exit passages 36 for passages into the discharge subchamber 28 and then out through the outlet passage 18 into the particle sizing sampler 11. It will be noted that the gas stream turns through a total of more than 180° up to 360° between the preimpaction jet passage 30 and the exit passages 36.

As the particles in the gaseous medium impact on the impaction plate 25, there is a tendency for some of these particles to bounce back off the impaction plate even though they are separated from the gaseous medium. This is especially true for dry particles with aerodynamic particle diameters well above the effective particle cut diameter of the preseparator 10. Further, there is a tendency to create a build-up of particles on the impaction plate 25 around the point of impaction and for agglomerated masses of these particles to be broken away from the point of impaction by the action of the gas stream. It has been found that slowing the gas stream velocity in the impaction subchamber after impaction to at least one-tenth of the impaction jet stream velocity and then not raising the velocity above about one-half the jet impaction velocity as the gas stream exits the impaction subchamber 26 minimizes the likelihood of these particles, after becoming separated, being reentrained in the gaseous medium flowing through the impaction subchamber 26. Preferably, the gas stream velocity in the impaction subchamber is reduced to at least about one-twentieth of the impaction jet stream velocity and does not rise above a velocity of about two-fifths of the jet impaction velocity as it exits the impaction subchamber. This is especially true where the height $h_E$ of the inlet ends 38 of passages 36 in exit tubes 35 is greater than the impaction distance $d_I$ and preferably about two times the distance $d_I$ so as to remove the inlet ends 38 out of the zone of separated particle movement in the vicinity of impaction plate 25. Also, because the exit velocity of the gas stream from subchamber 26 into the exit tubes 35 is maintained at one-half the jet impaction velocity or less, inadvertent separation of the particles still remaining in the gas stream onto the exit tubes 35 around the inlet ends 38 of exit passages 36 is minimized. Another factor which affects the particle separation of the gas stream is the residence time of the gas stream in the impaction subchamber 26. This is especially true with the agglomerated masses of particles broken away from the point of impaction by the action of the gas stream. The residence time of the gas stream in the impaction subchamber 26 must be sufficiently long to permit the agglomerated masses to settle out of the gas stream when they break away. This time should be a minimum of about 0.2 second. It is this combination of velocities, exit tube height and residence time which permits the preseparator to be used without distorting its performance characteristics.

The relative velocities between the gaseous medium in the jet impaction stream and the impaction subchamber in the vicinity of the impaction plate is determined by the cross-sectional area of the jet impaction passage 30 relative the net cross-sectional area of the impaction subchamber 26. Thus, the net cross-sectional area of the impaction subchamber 26 should be at least ten times that of the jet passage 30 in nozzle 20 and preferably at least twenty times that of the jet passage 30. Likewise, the relative velocities between the gaseous medium in the jet impaction stream and as it exits the impaction subchamber is determined by the cross-sectional area of the jet impaction passage 30 relative to the total cross-sectional area of the exit passages 36 in tubes 35. Thus, the total cross-sectional area of the exit passages 36 should be at least two times that of the jet passage 30 in nozzle 20 and preferably at least about two and one-half times that of jet passage 30. The residence time of the gaseous medium in the impaction subchamber 26 is dependent on the combination of the net cross-sectional area of the impaction subchamber 26, the height $h_E$ to the inlet ends 38 of exit passages 36 in tubes 35 and the volumetric flow rate of the gaseous medium through the preseparator. Thus, at a given volumetric flow rate, the net cross-sectional area of the impaction subchamber 26 and the height $h_E$ can be selected to maintain a minimum residence time of 0.2 second while at the same time maintaining the required gas velocity relationships required to satisfactorily operate the preseparator. The attached Table I sets forth one set of dimensions meeting these requirements.

TABLE I

| | |
|---|---|
| Impaction subchamber diameter $d_{PC}$ | 2.5 in. (6.35 cm) |
| Jet passage diameter $d_J$ | 0.48 in. (1.22 cm) |
| Impaction distance $d_I$ | 0.59 in. (1.50 cm) |
| Exit tube height $h_E$ | 1.19 in. (3.02 cm) |
| Exit passage diameter $d_{EP}$ | 0.44 in. (1.12 cm) |
| Ratios: | |
| $\frac{\text{Net impaction subchamber area}}{\text{Jet passage area}}$ | 22.2 |
| $\frac{\text{Total exit passage area}}{\text{Jet passage area}}$ | 2.5 |
| Under standard conditions of | 0.75 acfm and 70° F. |
| Impaction jet velocity | 9.75 ft/sec (297 cm/sec) |
| Impaction subchamber velocity | 0.44 ft/sec (13 cm/sec) |
| Exit passage velocity | 3.92 ft/sec (119 cm/sec) |
| Impaction subchamber residence time | 0.23 sec. |
| Effective particle cut diameter $D_{P50}$ | 11 microns |

SECOND EMBODIMENT

Figure 5:
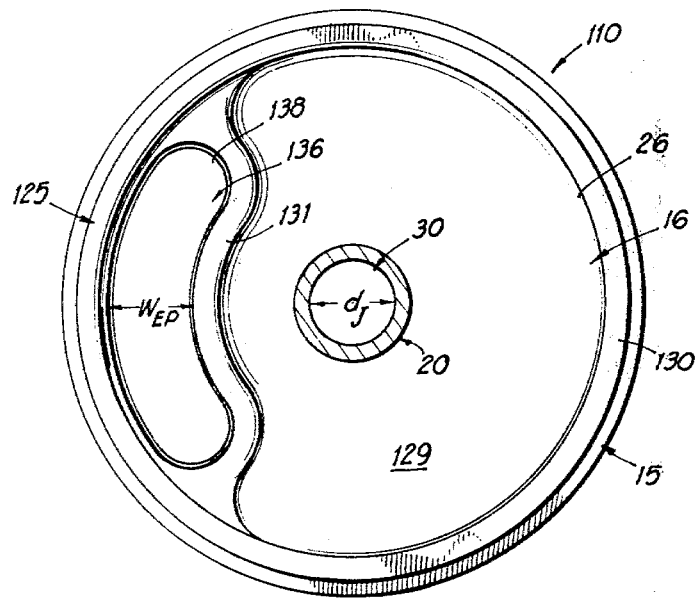
FIG. 5 is a transverse cross-sectional view taken along line 5—5 in FIG. 4.

A second embodiment of the impaction preseparator is illustrated in FIGS. 4 and 5 of the drawings. The second embodiment is designated generally by the numeral 110 and corresponds generally in size and function to the first embodiment of the impaction preseparator 10. Those components of the impaction preseparator 110 common to the impaction preseparator 10 have the same reference numerals applied thereto and will not be again described in detail. The difference between the impaction preseparator 10 and the impaction preseparator 110 lies in the arrangement of the impaction member and the exit passages which connect the impaction and discharge subchambers 26 and 28 in the preseparator chamber 16.

The impaction preseparator 110 includes a cup-shaped impaction member 125 which divides the preseparator chamber 16 into the impaction subchamber 26 and the discharge subchamber 28. The impaction member 125 has a generally circular end wall 126 oriented generally normal to the preseparator central axis $A_p$ and defining the preimpaction surface 129 thereon which faces the impaction outlet 34 in the preseparator impaction nozzle 20 and serves the same function as the preimpaction surface 29 in the impaction preseparator 10. The end wall 126 is integral with a generally cylindrical side wall 128 oriented concentrically about the axis $A_p$ and sized to be just received in the preseparator chamber 16. That end of the side wall 128 opposite the end wall 126 is provided with an outwardly directed locating lip 130 which fits between the end of the housing 15 and the cap 19 so that the impaction member 125 is held in place when the cap 19 is screwed onto the housing 15. This serves to locate the preimpaction surface 129 on the end wall 126 in the proper location for collecting the larger particles from the gas stream passing from the preseparator impaction nozzle 20 as described with respect to the preseparator 10.

The side wall 128 has an arcuate offset portion 131 formed therein through which is defined an arcuate exit passage 136 with a depending flange 135 therearound. The arcuate passage 136 has an inlet end 138 which is located the height $h_E$ above the preimpaction surface 129 in a manner corresponding to that of the impaction preseparator 10. It will be noted that the discharge subchamber 28 extends up behind the offset portion 131 in the side wall 128 so that the gas stream passes up after impaction against the preimpaction surface 129 and then out through the exit passage 136 between the depending flange 135 about the exit passage 136 into the discharge subchamber 28 for passage out of the preseparator 110. It will be seen that the exit passage 136 has a cross-sectional width $w_{EP}$ so that the effective cross-sectional area of the exit passage 136 is at least two times that of the cross-sectional area of the preimpaction jet passage 30 as was discussed with the preseparator 10 to maintain the gas stream velocity exiting subchamber 28 less than one-half the impaction jet velocity out of nozzle 20. The net cross-sectional area of the impaction subchamber 26 within the cup-shaped impaction member 125 is selected so that the velocity of the gaseous medium through the subchamber 26 is no more than one-tenth the impaction jet velocity out of nozzle 20. The net cross-sectional area of the impaction subchamber 26 and the height $h_E$ of the inlet to exit passage 136 are selected to maintain a gaseous medium residence time of at least 0.2 second in the impaction subchamber 26. The impaction preseparator 110 operates in accordance with the operation of the preseparator 10 described above.

The particle sizing sampler 11 as seen in FIGS. 1, 6 and 7 is illustrative of one type of a typical sampler with which the preseparator 10 or 110 is used. This sampler is known in the trade as a stack sampler primarily used to sample higher temperature gases in a stack discharging the gases into the atmosphere. The sampler 11 has a housing 50 concentric about sampler axis $A_S$ and defining a sampling chamber 51 therein connected to the outlet 18 of preseparator 10 or 110 via inlet 52. A jet impaction plate assembly 54 is carried in the sampling chamber 51 and includes a carrier 55 which mounts a plurality of perforated jet impaction plates 56 therein with annular seals 58 between each of the plates 56.

It will be noted that each of the perforated jet impaction plates 56 includes a plurality of jet impaction holes 59 therethrough with the holes 59 staggered from plate to plate as best seen in FIGS. 6 and 7. It will also be noted that the holes 59 decrease in diameter in the plates 56 as one moves downstream so that the entrained particles in the gaseous medium being sampled will be impacted onto the surface of the next lowermost plate 56 between the holes 59 therethrough as the gaseous medium passes therethrough. Because the holes 59 decrease in diameter as one moves downstream in the sampler 11, smaller and smaller particles will be separated from the gas stream by jet impaction on each plate 56 as one moves in this downstream direction through the sampler 11. The end of housing 50 opposite inlet 52 is provided with a discharge passage 60 which is connected to the conventional vacuum source (not shown).

The downstreammost plate 56 has no jet impaction holes but rather large gas outlet holes 61 as seen in FIGS. 6 and 7 to allow the gas to pass therethrough.

It will be appreciated that the preseparator 10 or 110 can be used with any type particle sizing sampler such as the high volume and low volume ambient air samplers as well as the viable particle samplers. The particular sampler 11 shown is for purposes of illustration only and is not intended to be limiting. It will also be appreciated that the relative size of the preseparator 10 or 110 will necessarily change with volumetric flow rate; however, the impaction velocities therein remain the same for the same particle size cut point, the relation between the impaction subchamber velocity and the impaction jet velocity will be maintained in the parameters set forth above, the relation between the exit velocity and the impaction jet velocity will be maintained in the parameters set forth above, and the residence time of the gaseous medium in the impaction subchamber will also be maintained in the parameters set forth above.

What is claimed as invention is:

1. A preseparator for connection to the sampling inlet of a particle sizing sampler so that a gaseous medium is forced first through the preseparator to preseparate those particles from the gaseous medium above the particle diameter acceptance range of the particle sizing sampler and then through the particle sizing sampler to separate those particles within the diameter acceptance range of the sampler from the gaseous medium according to size including:

a housing defining a preseparating chamber therein about a preimpaction central axis having an outlet therefrom connected to the sampling inlet of the particle sizing sampler;

an impaction plate mounted in said preseparating chamber and dividing said chamber into an impaction subchamber and a discharge subchamber, said outlet communicating with said discharge subchamber and the sampling inlet to the particle sizing sampler;

preimpaction nozzle means oriented generally normal to said impaction plate and defining at least one preimpaction jet passage therethrough having a nozzle inlet communicating with the gaseous medium to be sampled and a nozzle outlet communicating with said impaction subchamber, said nozzle outlet sized and located with respect to said impaction plate to cause those particles in the gaseous medium with effective particle diameters above the particle diameter acceptance range of the particle sizing sampler to be separated by jet impaction on said impaction plate within said impaction subchamber; and exit tube means defining at least one exit passage therethrough connecting said impaction subchamber with said discharge subchamber so that the gaseous medium passes from said impaction subchamber into said discharge subchamber through said exit passage, said exit passage having a passage inlet located in said impaction subchamber and spaced from said impaction plate a distance greater than the distance between said nozzle outlet of said preimpaction nozzle means and said impaction plate, the relative sizes of said nozzle outlet from said preimpaction jet passage and said impaction subchamber selected so that the velocity of the gaseous medium passing through said impaction subchamber is no greater than one-tenth of the velocity of the gaseous medium passing through said nozzle outlet from said preimpaction jet passage to permit the particles that bounce from said impaction plate upon impaction to be collected out of the gaseous medium within said impaction subchamber, the relative cross-sectional sizes of said passage inlet to said exit passage and said nozzle outlet from said preimpaction jet passage selected so that the velocity of the gaseous medium through said passage inlet to said exit passage is no greater than one-half of the velocity of the gaseous medium passing through said nozzle outlet from said preimpaction jet passage to prevent the motion of the gaseous medium flowing from said impaction subchamber into said passage inlet of said exit passage from dislodging and re-entraining particles which have already been separated in said impaction subchamber, and the distance between said passage inlet to said exit passage and said impaction plate together with the cross-sectional size of said impaction subchamber selected so that the residence time of the gaseous medium in said impaction subchamber is at least 0.2 second at the volumetric gas flow rate at which the preseparator is operated, to permit agglomerated particles dislodged after separation to settle out of the gaseous medium as it flows through said impaction subchamber.

2. The preseparator of claim 1 wherein said exit tube means includes a plurality of exit tubes mounted on said impaction plate and extending into said impaction subchamber, each of said exit tubes defining one of said exit passages therethrough communicating with said discharge subchamber, each of said exit passages in said exit tubes having a passage inlet located in said impaction subchamber and spaced from said impaction plate a distance at least two times the distance between said nozzle outlet and said impaction plate, said exit passages having a combined cross-sectional area at said passage inlets greater than two times the cross-sectional area of said nozzle outlet.

3. The preseparation of claim 2 wherein said exit tubes are oriented generally parallel to said preimpaction jet passage and each of said exit tubes are spaced from said preimpaction nozzle means by a center-to-center distance greater than the diameter of said nozzle outlet of said preimpaction jet passage to prevent said exit tubes from affecting the jet impaction characteristics of the gaseous medium impacting on said impaction plate.

4. The preseparator of claim 3 wherein said preimpaction nozzle means and said exit tubes are arranged to cause the gaseous medium to undergo a shift in flow direction greater than 180° from passage through said jet impaction passage to passage through said exit passages.

5. The preseparator of claim 4 wherein the net cross-sectional area of said impaction subchamber is at least twenty times the cross-sectional area of said nozzle outlet.

6. The preseparator of claim 5 wherein said exit passages have a combined cross-sectional area at said passage inlets at least 2.5 times the cross-sectional area of said nozzle outlet.

7. The preseparator of claim 1 wherein said passage inlet to said exit passage is spaced from said impaction plate a distance at least two times the distance between said nozzle outlet and said impaction plate; and wherein the relative sizes of said preimpaction jet passage and said impaction subchamber are selected so that the velocity of the gaseous medium passing through said impaction subchamber is no greater than one-twentieth of the velocity of the gaseous medium passing through said nozzle outlet from said preimpaction jet passage.

8. A preseparator for connection to the sampling inlet of a particle sizing sampler so that a gaseous medium is forced first through the preseparator to preseparate those particles from the gaseous medium above the particle diameter acceptance range of the particle sizing sampler and then through the particle sizing sampler to separate those particles within the diameter acceptance range of the sampler from the gaseous medium according to size including:

a housing defining a chamber therein about a preimpaction central axis, said chamber having an outlet therefrom connected to the sampling inlet of the particle sizing sampler and opening onto that end of said housing opposite said outlet;

a cap removably connected to that end of said housing onto which said chamber opens to close said chamber;

a cup-shaped impaction member removably mounted in said chamber in said housing and dividing said chamber into an impaction subchamber and a discharge subchamber with said outlet communicating with said discharge subchamber, said impaction member including an end wall oriented normal to the preimpaction central axis and a side wall connected to the periphery of said end wall, said side wall oriented generally concentrically of said preimpaction central axis and extending from said end wall toward said cap, said side wall including an offset portion therein, said offset portion defining an exit passage therethrough connecting said impaction subchamber with said discharge subchamber, said exit passage having an inlet end in said impaction subchamber; and a preimpaction nozzle mounted on said cap, said nozzle defining a preimpaction jet passage therethrough having a nozzle passage inlet communicating with the gaseous medium to be sampled and a nozzle passage outlet in said impaction subchamber, said jet passage oriented coaxially of the preimpaction central axis and normal to said end wall of said impaction member, said nozzle passage outlet sized and located with respect to said end wall of said impaction member to cause those particles in the gaseous medium with effective particle diameters above the particle diameter acceptance range of the particle sizing sampler to be separated by jet impaction on said end wall of said impaction member within said impaction subchamber, said inlet end of said exit passage spaced from said end wall a distance greater than the distance between said nozzle outlet of said preimpaction nozzle means and said end wall, the relative sizes of said nozzle passage outlet of said preimpaction jet passage and said impaction subchamber selected so that the velocity of the gaseous medium passing through said impaction subchamber is no greater than one-tenth of the velocity of the gaseous medium passing through said nozzle passage outlet from said preimpaction jet passage to permit particles that bounce from said end wall upon impaction to be collected out of the gaseous medium within said impaction subchamber, the relative cross-sectional sizes of said inlet end to said exit passage and said nozzle passage outlet from said preimpaction jet passage selected so that the velocity of the gaseos medium through said inlet end to said exit passage is no greater than one-half the velocity of the gaseous medium passing through said nozzle passage outlet from said preimpaction jet passage to prevent the motion of the gaseous medium flowing from said impaction subchamber into said passage inlet of said exit passage from dislodging and re-entraining particles which have already been separated in said impaction subchamber, and the distance between said inlet end of said exit passage and said end wall together with the cross-sectional size of said impaction subchamber selected so that the residence time of the gaseous medium in said impaction subchamber is at least 0.2 second at the volumetric gas flow rate at which the preseparator is operated to permit agglomerated particles dislodged after separation to settle out of the gaseous medium as it flows through said impaction subchamber.

9. The preseparator of claim 8 wherein said impaction member further includes a support flange connected to said side wall and removable received between said housing and said cap to support said impaction member in said chamber.

10. The preseparator of claim 9 wherein said impaction member further includes a flange integral with said offset portion around said inlet end of said exit passage and extending into said discharge subchamber to define said exit passage therethrough.

* * * * *

Disclaimer 4,255,172.—*Michael L. Smith*, Atlanta, Ga. JET IMPACTION PRE-SEPARATOR. Patent dated Mar. 10, 1981. Disclaimer filed Jan. 25, 1982, by the assignee, *Andersen Samplers, Inc.*

Hereby enters this disclaimer to all claims of said patent.

[*Official Gazette September 14, 1982.*]